United States Patent [19]

Farng et al.

[11] Patent Number: 4,906,393

[45] Date of Patent: Mar. 6, 1990

[54] MIXED PHENOL/DIMERCAPTOTHIADIAZOLE-DERIVED HYDROXYTHIOETHER BORATES AS ANTIOXIDANT/ANTIWEAR MULTIFUNCTIONAL ADDITIVES

[75] Inventors: Liehpao O. Farng, Lawrenceville; Andrew G. Horodysky; William F. Olszewski, both of Cherry Hill, all of N.J.

[73] Assignee: Mobil Oil Corporation, New York, N.Y.

[21] Appl. No.: 292,168

[22] Filed: Dec. 30, 1988

[51] Int. Cl.$^4$ .......................................... C10M 135/36
[52] U.S. Cl. .................. 252/47.5; 252/49.6; 252/400.4; 252/402; 548/142; 548/135; 548/129
[58] Field of Search ................... 252/47.5, 49.6, 400.4, 252/402; 548/142, 135, 129

[56]  References Cited

U.S. PATENT DOCUMENTS

| 4,273,665 | 6/1981 | Braid et al. | 252/49.6 |
| 4,298,486 | 11/1981 | Horodysky et al. | 252/49.6 |
| 4,370,248 | 1/1983 | Horodysky et al. | 252/49.6 |
| 4,582,617 | 4/1986 | Doner et al. | 252/49.6 |
| 4,584,114 | 4/1986 | Gemmill et al. | 252/47.5 |
| 4,584,115 | 4/1986 | Davis | 252/49.6 |
| 4,661,273 | 4/1987 | Frangatos et al. | 252/47.5 |
| 4,761,482 | 8/1988 | Karol | 252/47.5 |
| 4,800,028 | 1/1989 | Toukan | 252/49.6 |

Primary Examiner—Jacqueline V. Howard
Attorney, Agent, or Firm—Alexander J. McKillop; Charles J. Speciale; Howard M. Flournoy

[57] ABSTRACT

Mixed phenol/dimercaptothiadiazole-derived hydroxythioether borates have been found to be effective antiwear/antioxidant multifunctional additives for lubricants.

28 Claims, No Drawings

MIXED PHENOL/DIMERCAPTOTHIADIAZOLE-DERIVED HYDROXYTHIOETHER BORATES AS ANTIOXIDANT/ANTIWEAR MULTIFUNCTIONAL ADDITIVES

BACKGROUND OF THE INVENTION

This application is directed to lubricant compositions containing small additive concentrations of phenolic/-dimercaptothiadiazole-derived hydroxythioether borates which possess excellent antioxidant properties as well as very good antiwear and extreme pressure/load carrying characteristics.

The use of phenolic compositions such as nonylphenol, and especially hindered phenols, such as di-tertiary butyl paracresol and, has been well-known for imparting antioxidant properties to a variety of lubricant, polymer and elastomer applications.

The use of 2,5-dimercapto 1,3,4-thiadiazole and its derivatives has found widespread application as multifunctional lubricant anticorrision, antiwear, antioxidant and copper passivation additives, see U.S. Pat. Nos. 4,661,273 and 4,584,114.

The use of borate esters has been widely reported as having beneficial multifunctional and friction reducing properties. For example borates and borate esters are disclosed in RE 37,295 and in U.S. Pat. Nos. 4,370,248; 4,298,486 and 4,273,665.

It has now been found that the use of phenolic/dimercaptothiadiazole-derived hydroxythioether borates provides exceptional antioxidant and antiwear/EP activity with potential corrosion inhibiting, antifatigue and high temperature stabilizing properties.

SUMMARY OF THE INVENTION

The use of additive concentrations of phenolic/-dimercaptothiadiazole-derived hydroxythioether borates in premium quality automotive and industrial lubricants will significantly enhance their stability, and extend the service life as well as reduce wear. The novel compositions is described herein below are useful at low concentrations and do not contain any potentially undesirable metals, phosphorus or chlorine, and can be readily made commercially under favorable economic conditions.

Generally speaking and in accordance with the invention, there are provided (1) a product made by reacting a dimercaptothiadiazole with an alkylene oxide forming a dimercaptothiadiazole-derived alcohol, which is then co-borated with a phenolic alcohol to form the novel mixed borate esters of this invention and (2) a lubricant composition comprising a major amount of an oil of lubricant viscosity or grease prepared therefrom and a minor effective multifunctional amount of said product.

DESCRIPTION OF SPECIFIC EMBODIMENTS

Both the phenolic moiety and the dimercaptothiadiazole moiety are believed to provide the basis for the synergistic antioxidant activity each of which are subsequently enhanced by the integral boron coupling moiety. The dimercaptothiadiazole-derived hydroxythioether group is also believed to contribute additional antiwear/EP properties to these novel additives. The boron moieties may additional contribute significant antifatigue and/or high temperature stabilizing properties to this new class of additives.

All of these beneficial properties are believed to be enhanced as a result of this novel internal synergism. This unique internal synergism concept is believed to be applicable to similar structures containing (a) phenolic groups, (b) dimercaptothiadiazole-derived hydroxythioether groups, and (c) borate ester linkages within the same molecule. The products of this patent application show good stability and compatability when used in lubricant compositions in the presence of other commonly used additives.

In general for example, the products of reaction are prepared as follows: 2,5-dimercapto 1,3,4-thiadiazole (made by the reaction of hydrazine and carbon disulfide) was reacted with alkylene oxide to form dimercaptothiadiazole-derived alcohols (eqn. 1). These alcohols were then co-borated with phenols and/or phenolic alcohols to form mixed borate esters (eqn. 2 or 3), as generally described below:

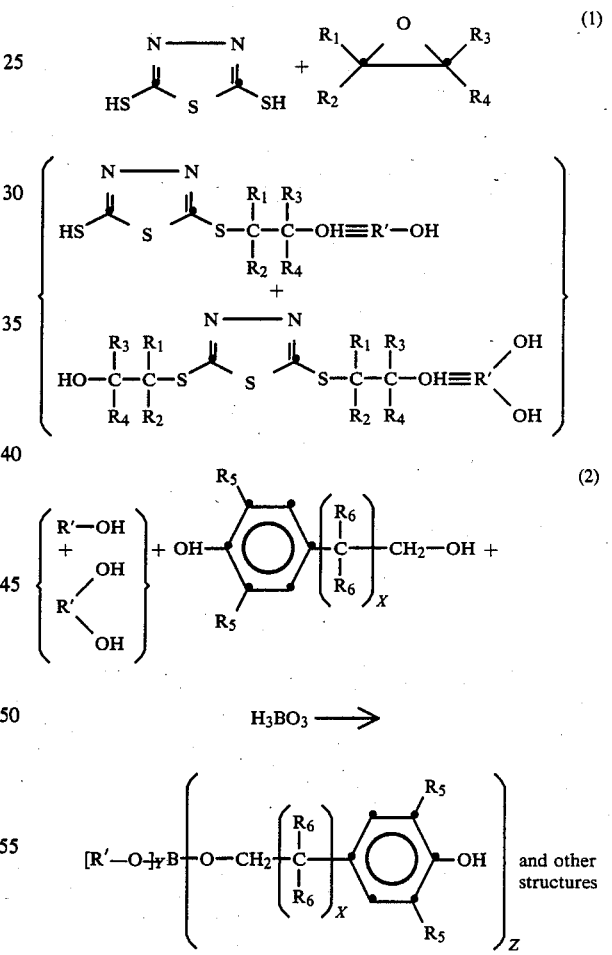

where

R$_1$, R$_2$, R$_3$, and R$_4$ are hydrogen, or C$_1$ to C$_{60}$ hydrocarbyl, and can optionally contain sulfur, nitrogen and/or oxygen.

R' represents the dimercaptothiadiazole-derived moiety.

R$_5$ is hydrogen or C$_1$ to C$_{20}$ hydrocarbyl, and can optionally contain S, N and/or O.

$R_6$ is hydrogen or $C_1$ to $C_{10}$ hydrocarbyl, and can optionally contain S, N and/or O.

X is 0 to 10

Y and Z are integers and Y+Z=3.

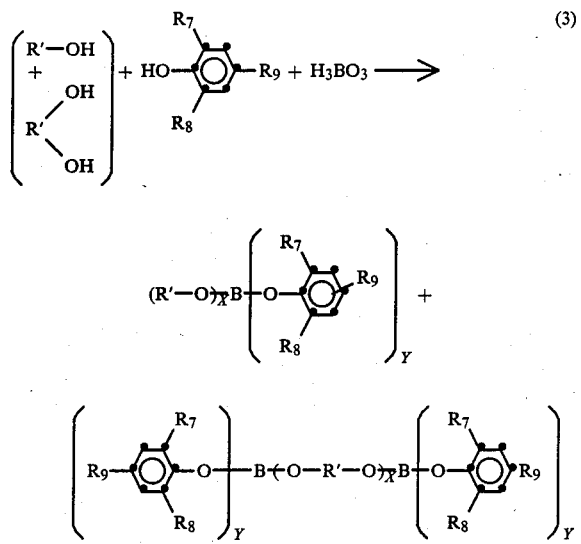

Preferred phenols are:

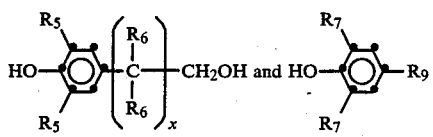

where $R_7$ and $R_8$ are hydrogen, or $C_1$ to $C_{20}$ hydrocarbyl, and $R_9$ is hydrogen or a $C_1$ to $C_{30}$ hydrocarbyl group. $R_7$, $R_8$ and/or $R_9$ can optionally contain S, N, and/or O. X and Y are integers, and X+Y=3.

Any appropriate mercapto-thiadiazole may be used herein. However, preferred is 2,5-dimercapto-1,3,4-thiadiazole. Some suitable examples include but are not limited to 3,4-dimercapto-1,2,5-thiadiazole, 3,5-dimercaptobenzo 1,2,3-thiadiazole, 4,7-dimercaptobenzo 1,2,3-thiadiazole, 4,6-dimercaptobenzol 1,2,3-thiadiazole, 5,6-dimercaptobenzo 1,2,3-thiadiazole, 5,7-dimercaptobenzo 1,2,3-thiadiazole, 6,7-dimercaptobenzo 1,2,3-thiadiazole, 4,5-dimercaptobenzo 2,1,3-thiadiazole, 4,6-dimercaptobenzo 2,1,3-thiadiazole, 5,6-dimercaptobenzo 2,1,3-thiadiazole, 5,7-dimercaptobenzo 2,1,3-thiadiazole, 6,7-dimercaptobenzo 2,1,3-thiadiazole.

Suitable alkylene oxides are of the formula described in Equation 1 above. Preferred is 1,2-epoxybutane. However, included with the scope of the epoxides as set forth in Equation 1 are 1,2-epoxydecane, 1,2-epoxydodecane, 1,2-epoxytetradecane, 1,2-epoxypentadecane, 1,2-epoxyhexadecane, 1,2-epoxyheptadecane, 1,2-epoxyoctadecane, 1,2-epoxyeicosane, 1,2-epoxybutane and mixtures of such epoxides.

Hydrocarbyl as used herein includes but is not limited to alkyl, aryl, alkaryl, aralkyl, alkenyl cycloalkyl or cycloakenyl groups containing from 8 to 30 carbon atoms, preferably 10 to 22 carbon atoms.

An excess of one reagent or another can be used. Molar quantities, less than molar quantities or more than molar quantities of a boronating agent can be used.

The reactions can, broadly be carried out over a wide range of temperatures from about 50° C. to about 300° C. in from about 0.5 an hour to about 10 hours, depending on temperature and reactivity of the reactants. For specific reactions, the temperatures of reaction can be from about 50° C. to about 250° C., preferably about 100° C. to about 200° C. for the reaction between the DMTD and the alkylene oxide.

When carrying out the reaction between the DMTD derived alcohols and the phenolic alcohols and the boronating agent the temperature will generally be from about 100° C. to about 300° C., preferably about 150° C. to about 275° C. Times will run from about one hour or less to about ten (10) hours. However, the boration can be carried out in any convenient manner or sequence and under any conditions known in the art.

Solvents are preferred in carrying out the invention. Broadly, any solvent can be used that does not react and is a solvent for all the reactants and the reaction product and can be removed easily or is compatible with the environment in which the product will be used. Hydrocarbon solvents such as toluene, benzene, xylenes are preferred for the reactions.

The borating agent can be boric acid or a compound of the formula $$(RO)_p(BO_2)_q ZrY$$

where R, Y and Z are hydrogen or alkyl groups of from 1 to about 6 carbon atoms, p and r are 0 to 2 and q is 1 to 3. The useful boronating compounds covered by the above formula include boric acid, metaboric acid, alkyl metaborates, alkyl boroxines, boroxine boroxides, and the like, as well as alkyl and trialkyl borates. Nevertheless, any suitable boronating agent may be used. Preferably the boration is carried out in substantially stoichiometric ratios of reactants. However, an excess of boronating agent is on occasion desirable.

The phenolic alcohols are preferably hindered phenolic alcohols as defined hereinabove in equation (2). However, any suitable phenolic alcohol may be used herein as for example nonyl phenolic alcohol. Any phenol or hydrocarbyl phenol or sulfurized hydrocarbyl-substituted phenol can be also be used.

While the reaction sequence has been disclosed to be reaction of (1) a dimercaptothiadiazole and (2) an alkylene oxide, (3) a hydroxyalkylphenol or phenol and (4) the invention is not limited to that method sequence. The boronation may take place at any convenient point. Furthermore, all reactants can be mixed and reacted in one step, in which case the temperature again can be from about 50° C. to about 300° C. and the time from about 0.5 hour to about ten (10) hours.

The products of the invention are used in minor multifunctional antioxidant/antiwear or anticorrosion amounts with a major proportion of a lubricating oil or grease. In general, this will amount to from about 0.25% to about 15% by weight of the total composition. Furthermore, other additives, such as other detergents, antioxidants, antiwear agents and the like may be present. These can include phenates, sulfonates, succinimides, zinc dithiophosphates, polymers, calcium and magnesium salts and the like.

A most important feature of the invention is the ability of the additive to improve the resistance to oxidation of oleaginous materials such as lubricating oils, either a mineral oil or a synthetic oil, or mixtures thereof, or a grease in which any of the aforementioned oils are employed as a vehicle. In general, mineral oils, both paraffinic, naphthenic and mixtures thereof, employed as a lubricating oil or as the grease vehicle, may be of any suitable lubricating viscosity range, as for example, for about 45 SSR at 100° F. to about 6000 SSU at 100° F., and preferably from about 50 to about 250 SSR at 210° F. These oils may have viscosity indexes ranging to about 100 or higher. Viscosity indices from about 70 to about 95 are preferred. The average molecular weights of these oils may range from about 250 to about 800. Where the lubricant is to be employed in the form of a grease, the lubricating oil is generally employed an amount sufficient to balance the total grease composition, after accounting for the desired quantity of the thickening agent, and other additive components to be included in the grease formulation.

A wide variety of materials may be employed as thickening or gelling agents. These may include any of the conventional metal salts or soaps, including calcium or lithium soaps which include calcium or lithium stearates or calcium or lithium hydroxystearates. These are dispersed in the lubricating vehicle in grease-forming quantities in the amount to impart to the resulting grease composition the desired consistency. Other thickening agents that may be employed in the grease formulation may comprise the non-soap thickeners, such as surface-modified clays and silicas, aryl ureas, calcium complexes and similar materials. In general, grease thickeners may be employed which do not melt and dissolve when used at the required temperature within a particular environment; however, in all other respects, any material which is normally employed for thickening or gelling hydrocarbon fluids for forming grease can be used in preparing the aforementioned improved grease in accordance with the present invention.

As noted hereinabove, the lubricants contemplated for use with the products herein disclosed include mineral and synthetic hydrocarbon oils of lubricating viscosity, mixtures of mineral oils and synthetic oils, including mixtures. The synthetic hydrocarbon oils include long-chain alkanes such as cetanes and olefin polymers such as oligomers of hexene, octene, decene, and dodecene, etc. The products of this invention are especially effective in synthetic oils formulated using mixtures of synthetic hydrocarbon olefin oligomers and lesser amounts of hydrocarbyl carboxylic ester fluids. Other synthetic oils, which can be mixed with a mineral or synthetic hydrocarbon oil, include (1) fully esterified ester oils, with no free hydroxyls, such as pentaerythritol esters of monocarboxylic acids having 2 to 20 carbon atoms, timethylolpropane esters of monocarboxylic acids having 2 to 20 carbon atoms, (2) polyacetals and (3) siloxane fluids. Especially useful among the synthetic esters are those made from polycarboxylic acids and monohydric alcohols. More preferred are the ester fluids made by fully esterifying pentaerythritol, or mixtures thereof with di- and tripentaerythritol, with an aliphatic monocarboxylic acid containing from 1 to 20 carbon atoms, or mixtures of such acids.

Having described the invention with reference to its broader aspects, the following are offered to specifically illustrate it. It will be understood that the Examples are for illustration only and are not intended to limit the scope of the invention.

EXAMPLE 1

Dimercaptothiadiazole-Vikolox 12 Reaction Adduct

Approximately 225 grams of 2,5-dimercapto 1,3,4-thiadiazole (1.5 mole commercially obtained) was suspended in 400 milliliters of toluene in a two-liter flask and slowly 553 grams of Vikolox 12 (3.0 mole, commercially obtained from Viking Chemical Company $C_{12}$ epoxidized alpha olefin with minimum Oxirane 9.2% and general formula $C_{12}H_{24}O$) was added over a course of four hours at 70° to 75° C. The reactants were further heated at 75° C. for two additional hours after the completion of Vikolox addition, and thereafter at 113° C. for four extra hours. The toluene was removed by vacuum distillation to produce about 764 grams of a viscous, brown waxy material containing 16.2% sulfur (Theory 18.6%).

EXAMPLE 2

Mixed 2,6-Di-t-Butyl-4-Hydroxymethylphenol/Dimercaptothiadiazole-derived Hydroxythioether Borates Approximately 129.7 grams of the above product of Example 1, 118 grams of 2,6-di-tertiary-butyl-4-hydroxymethylphenol (commercially obtained as Ethanox 754), 20.7 grams boric acid (0.33 mole), 200 milliliters of toluene were mixed together in a one-liter, four-neck reactor equipped with thermometer, $N_2$ sparger, and Dean-Stark trap condenser and agitator. This mixture was refluxed at boiling toluene (113±2° C.) over a course of eight hours. A total amount of 17.3 milliliters of water was collected in the Dean-Stark trap.

Thereafter, the volatiles were removed by distillation to leave about 263.5 grams of a viscous, reddish-brown material containing 1.1% boron, and 11.2% sulfur (Theory 9.3%).

EXAMPLE 3

Mixed Nonylphenol/Dimercaptothiadiazole-derived Hydroxythioether Borates

Approximately 129.7 grams of the above product of Example 1, 221.3 grams of nonylphenol (1.0 mole), 31.2 grams of boric acid (0.508 mole), 350 milliliters of toluene are mixed together in a two-liter, four-neck reactor. This mixture is refluxed at 118±2° C. over a course of nine hours. A total amount of 21.7 milliliters of water is collected in the Dean-Stark trap. An additional hour of heating will produce no more water or reaction. Then the volatiles are removed by distillation at reduced pressure to produce about 373 grams of a viscous, brown material containing 1.2% of boron and 5.5% of sulfur (Theory 1.46% boron, 6.4% sulfur).

The mixed borates were blended into fully formulated minerals oils and evaluated for antioxidant performance by Catalytic Oxidation Test at 325° F. for 40 hours (Table 1); Catalytic Oxidation Test at 375° F. for 24 hours (Table 2).

Catalytic Oxidation Test

Basically, the test lubricant is subjected to a stream of air which is bubbled through at the rate of five liters per hour respectively at 325° F. for 40 hours and at 375° F. for 24 hours. Present in the composition are samples of metals commonly used in engine construction, namely, iron, copper, aluminum, and lead. See U.S. Pat. No.

3,682,980, incorporated herein by reference, for further details of the test.

TABLE 1

Catalytic Oxidation Test 40 Hours at 325° F.

| Item | Additive Conc. (wt %) | Percent Change in Acid Number Δ TAN | Percent Change in Viscosity Δ KV, % |
| --- | --- | --- | --- |
| Base Oil (150 second, fully formulated, solvent refined paraffinic bright oil containing deformant/demulsifier/antiwear/anticorrosion/EP/antirust performance package. | — | 2.58 | 30.61 |
| Example 3 | 1.0 | 0.92 | 27.73 |

TABLE 2

Catalytic Oxidation Test 24 Hours at 375° F.

| Item | Additive Conc. (wt %) | Change in Acid Number Δ TAN | Percent Change Viscosity Δ KV, % | Sludge |
| --- | --- | --- | --- | --- |
| Base Oil (150 second, fully formulated, solvent refined paraffinic bright oil containing deformant/demulsifier/antiwear/anticorrosion/EP/antirust performance package. | — | 6.53 | 117.9 | Medium |
| Example 2 | 1.0 | 3.88 | 103.9 | Trace |
| Example 3 | 1.0 | 3.43 | 100.5 | Trace |

The mixed phenolic/dimercaptothiadiazole-derived hydroxythioether borates were evaluated for antiwear performance using the Four-Ball Test in minerals oils. In the Four-Ball Wear Test using a 60 kg load at respectively 1000 rpm at 200° F., 2000 rpm at 200° F. and 1000 rpm at 300° F., for thirty minutes as shown in Table 3.

Four-Ball Wear Test

Three stationary balls are placed in the lubricant cup and the lubricant containing the compound to be tested is added thereto, and a fourth ball is placed in a chuck mounted on a device which can be used to spin the ball at known speeds and loads. The samples were tested using ½ inch stainless steel balls of 52100 steel for 30 minutes.

TABLE 3

Four-Ball Test
Wear Scar Diameter in MM, 30 Minute/Test 60 kg Load

| Item | 1000 rpm 200° F. | 2000 rpm 200° F. | 1000 rpm 300° F. |
| --- | --- | --- | --- |
| Base oil (80% solvent paraffinic bright, 20% solvent paraffinic neutral mineral oils) | 1.91 | 2.63 | 1.95 |
| 1% Example 3 in above Base Oil | 0.65 | 0.94 | 0.98 |

As shown above, the products of this invention show considerable antiwear and antioxidant activity.

The products of described examples were also blended into formulated synthetic oils and evaluated for antioxidant performance by the Oxidation and Corrosion Test at 400° F. for 72 hours (Table 4), for antiwear performance by Four-Ball Wear Test and SAE Wear Test (Table 5).

TABLE 4

Oxidation and Corrosion Test (400° F., 72 Hours)

| Item | Base Oil (pentaerythritol esters) | Test Oil One Containing 0.25% wt % Additive of Example 2 | Test Oil Two Containing 0.25 wt % Additive of Example 3 | Targets |
| --- | --- | --- | --- | --- |
| Percent change in Viscosity Δ KV, % | 388 | 10.53 | 11.59 | 25 max. |
| Percent Change in Acid Number Δ TAN | 12.22 | 1.17 | 1.50 | 3 max. |
| Metals | | | | |
| Al | 0 | 0 | −0.0001 | ±0.2 mg/cm$^2$ |
| Ag | −0.0003 | −0.0002 | −0.0002 | ±0.2 mg/cm$^2$ |
| Cu | −0.0125 | −0.0012 | −0.0010 | ±0.2 mg/cm$^2$ |
| Steel | −0.0001 | +0.0001 | −0.0002 | ±0.2 mg/cm$^2$ |
| Mg | −0.2164 | +0.0002 | −0.0002 | ±0.2 mg/cm$^2$ |
| Sludge | | | | |
| vapor | medium | trace/light | trace/light | |
| interface | heavy | trace | trace/light | |
| liquid | heavy | nil | trace | |

TABLE 5

| Item | SAE Wear (400 lbs 275° F., 156 RPM) | Four Ball (20 kg, 130° 20 1800 RPM, 60 Minutes) Wear Scar (MM) |
| --- | --- | --- |
| Base oil (pentaerythritol ester containing antioxidant, defoamant, anticorrosion, EP performance package) | Fail | 0.492 |
| Fully formulated synthetic esters containing 0.25% Example 2 | Pass | 0.271 |
| Fully formulated synthetic esters containing 0.25% Example 3 | Pass | 0.263 |

As can be seen from the above test results, the products described completely satisfy and meet the desired specifications.

Although the present invention has been described with preferred embodiments, it is to be understood that modifications and variations may be resorted to, without departing from the spirit and scope of this invention, as those skilled in the art will readily understand. Such modifications and variations are considered to be within the purview and scope of the appended claims.

We claim:

1. A product of reaction made by reacting in any convenient reaction sequence (1) a dimercaptothiadiazole of the formula:

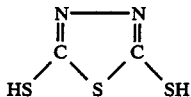

with (2) an alkylene oxide of the formula:

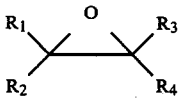

where $R_1$, $R_2$, $R_3$ and $R_4$ are each independently H, or $C_1$ to about $C_{60}$ hydrocarbyl and can optionally contain S, N, and/or O, (3) a phenolic compound, and (4) a suitable boronating agent in substantially equimolar, less than molar or more than molar amounts said reaction temperatures varying from about 50° to about 300° C. and said reaction times varying from about 0.5 to about 10 hours.

2. The product of claim 1 wherein said thiadiazole is 2,5-dimercapto 1,3,4-thiadiazole.

3. The product of claim 1 wherein hydrocarbyl is selected for the group consisting of alkyl, alkenyl, aryl, aralkyl, alkaryl, cycloalkyl, cycloalkenyl and mixtures thereof.

4. The product of claim 1 wherein the boronating agent is selected from the group consisting of boric acid and a compound of the formula $$(RO)_p(BO_2)_qZrY$$

wherein R, Y and Z are individually hydrogen or alkyl groups of from 1 to about 6 carbon atoms and p and r are each separately 0 to 2 and q is 1 to 3.

5. The product of claim 4 wherein the boronating agent is boric acid.

6. The product of claim 1 wherein the phenolic compound is selected from the group consisting of alkylated phenols, sulfurized phenols and hydroxyalkyl phenols, optionally containing sulfur, nitrogen and/or oxygen.

7. The product of claim 1 wherein the phenolic compound is a hindered phenol.

8. The product of claim 7 wherein the phenolic compound is 2,6-ditertiary-butyl-4-hydroxymethylphenol.

9. The product of claim 1 wherein the phenolic compound is a non-hindered phenol.

10. The product of claim 9 wherein the phenolic compound is nonylphenol.

11. The product of claim 1 wherein the alkylene oxide is a $C_{12}$ epoxidized alpha olefin.

12. A lubricant composition comprising a major poroporation of a lubricating oil or grease prepared therefrom and an effective multifunctional amount of a product of reaction made by reacting in any convenient reaction sequence or (1) dimercaptothiadiazole of the formula:

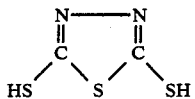

with (2) an alkylene oxide of the formula:

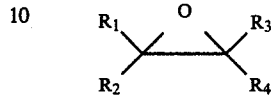

where $R_1$, $R_2$, $R_3$ and $R_4$ are each independently H, or $C_1$ to about $C_{60}$ hydrocarbyl and can optionally contain S, N, and/or O, and (3) a phenolic compound, (4) a suitable boronating agent in substantially equimolar, less than molar or more than molar amounts and where reaction temperatures vary from about 50° to about 300° C. and said reaction times vary from about 0.5 to about 10 hours.

13. The composition of claim 12 wherein said thiadiazole is 2,5-dimercapto 1,3,4-thiadiazole.

14. The composition of claim 12 wherein hydrocarbyl is selected for the group consisting of alkyl, alkenyl, aryl, aralkyl, alkaryl, cycloalkyl, cycloalkenyl and mixtures thereof.

15. The composition of claim 12 wherein the boronating agent is selected from the group consisting of boric acid and a compound of the formula $$(RO)_p(BO_2)_qZrY$$

wherein R, Y and Z are hydrogen or alkyl groups of from 1 to about 6 carbon atoms and p and r are each individually 0 to 2 and q is 1 to 3.

16. The composition of claim 15 wherein the boronating agent is boric acid.

17. The composition of claim 12 wherein the phenolic compound is selected from the group consisting of alkylated phenols, sulfurized alkylated phenols and alkoxylated phenols.

18. The composition of claim 17 wherein the phenolic compound is a hindered phenol.

19. The composition of claim 17 wherein the phenolic compound is a non-hindered phenol.

20. The composition of claim 18 wherein the phenolic compound is 2,6-ditertiary-butyl-4-hydroxymethylphenol.

21. The composition of claim 19 wherein the phenolic compound is nonylphenol.

22. The composition of claim 12 wherein the alkylene oxide is a $C_{12}$ epoxidized alpha olefin.

23. The composition of claim 12 wherein the lubricant is an oil of lubricating viscosity, selected from the group consisting of (1) mineral oils, (2) synthetic oils or a mixture of synthetic oils, (3) mixture of (1) and (2) or (4) a grease prepared from (1), (2), or (3).

24. The composition of claim 23 wherein said oil is a mineral oil.

25. The composition of claim 23 wherein said oil is a synthetic oil.

26. The composition of claim 23 wherein the lubricant is a grease.

27. A process of making a product suitable for use as a lubricant additive comprising reacting in any convenience reaction sequence or (1) dimercaptothiadiazole of the formula:

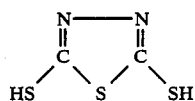

with (2) an alkylene oxide of the formula:

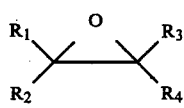

where $R_1$, $R_2$, $R_3$ and $R_4$ are each independently H, or $C_1$ to about $C_{60}$ hydrocarbyl and can optionally contain S, N, and/or O, (3) a phenolic compound, and (4) a suitable boronating agent in substantially equimolar, less than molar or more than molar amounts, said reaction temperatures varying from about 50° to about 300° C. and said reaction times varying from about 0.5 to about 10 hours.

28. The process of claim 27 wherein the boronating agent is selected from the group consisting of boric acid and a compound of the formula:

$$(RO)_p(BO_2)_qZrY$$

wherein R, Y and Z are individually hydrogen or alkyl groups of from 1 to about 6 carbon atoms, p and r are each separately 0 to 2 and q is 1 to 3.

* * * * *